(12) United States Patent
Clark et al.

(10) Patent No.: US 7,292,898 B2
(45) Date of Patent: Nov. 6, 2007

(54) METHOD AND APPARATUS FOR REMOTELY MONITORING AND CONTROLLING A POOL OR SPA

(75) Inventors: Tim Clark, Mill Valley, CA (US); Stephen J. Scherer, Tustin, CA (US); Paul A. Rosenau, Santa Ana, CA (US)

(73) Assignee: Balboa Instruments, Inc., Tustin, CA (US)

( * ) Notice: Subject to any disclaimer, the term of this patent is extended or adjusted under 35 U.S.C. 154(b) by 20 days.

(21) Appl. No.: 09/872,133

(22) Filed: Jun. 1, 2001

(65) Prior Publication Data

US 2002/0035403 A1    Mar. 21, 2002

Related U.S. Application Data

(60) Provisional application No. 60/233,376, filed on Sep. 18, 2000.

(51) Int. Cl.
*G06F 23/02* (2006.01)
*G06F 11/00* (2006.01)
*G06F 15/00* (2006.01)
*G05B 15/02* (2006.01)
*G05B 11/01* (2006.01)

(52) U.S. Cl. .................. 700/9; 700/17; 700/19; 700/20; 700/83; 700/275; 340/3.1; 702/188

(58) Field of Classification Search ............ 700/19–20, 700/2, 3, 83, 86–87, 9, 17, 275; 340/825.06, 340/3.1; 702/188
See application file for complete search history.

(56) References Cited

U.S. PATENT DOCUMENTS

| | | | |
|---|---|---|---|
| 5,117,233 A * | 5/1992 | Hamos et al. ......... | 340/825.69 |
| 5,326,481 A | 7/1994 | Alwerud | |
| 5,351,215 A | 9/1994 | Tanabe | |
| 5,550,753 A | 8/1996 | Tompkins et al. | |
| 5,559,720 A | 9/1996 | Tompkins et al. | |
| 5,572,438 A * | 11/1996 | Ehlers et al. ............... | 700/295 |
| 5,616,239 A * | 4/1997 | Wendell et al. ............... | 210/86 |
| 5,730,861 A | 3/1998 | Sterghos et al. | |
| 5,781,108 A | 7/1998 | Jacob et al. | |
| 5,895,565 A | 4/1999 | Steininger et al. | |
| 5,917,405 A * | 6/1999 | Joao ...................... | 340/426.17 |
| 5,959,534 A | 9/1999 | Campbell et al. | |

(Continued)

OTHER PUBLICATIONS

Webpage located at, "http:www.ibutton.com/TINI/software/index. html" entitled, TINI Software, printed on Oct. 25, 2000 (2 pages).

(Continued)

*Primary Examiner*—Ronald D Hartman, Jr.
(74) *Attorney, Agent, or Firm*—Larry K. Roberts

(57) ABSTRACT

A system for remotely monitoring and/or controlling a pool or spa. The remote control can utilize a microprocessor-based data acquisition and processing system, along with a network interface, to provide remote access to the pool or spa parameters, including but not limited to: temperature, pH, and ORP levels; and the status and control of pumps, heaters, ozone apparatus, and filters. The information is presentable via the Internet, a private or other networks, and can be accessed through known browsers or other convenient interfaces, allowing for operation across all computing platforms.

18 Claims, 16 Drawing Sheets

U.S. PATENT DOCUMENTS

| | | | |
|---|---|---|---|
| 5,960,411 | A | 9/1999 | Hartman et al. |
| 6,003,164 | A | 12/1999 | Leaders |
| 6,023,223 | A | 2/2000 | Baxter, Jr. |
| 6,058,355 | A * | 5/2000 | Ahmed et al. ............... 702/62 |
| 6,124,806 | A * | 9/2000 | Cunningham et al. . 340/870.02 |
| 6,125,481 | A | 10/2000 | Sicilano |
| 6,160,477 | A | 12/2000 | Sandelman et al. |
| 6,192,282 | B1 * | 2/2001 | Smith et al. ................. 700/19 |
| 6,363,422 | B1 * | 3/2002 | Hunter et al. ............... 709/224 |
| 6,374,079 | B1 * | 4/2002 | Hsu ........................ 455/11.1 |
| 6,549,130 | B1 * | 4/2003 | Joao ...................... 340/539.14 |
| 6,782,309 | B2 * | 8/2004 | Laflamme et al. .......... 700/275 |
| 2003/0109938 | A1 * | 6/2003 | Daum et al. ................. 700/11 |

OTHER PUBLICATIONS

Webpage entitled, "Aqualink RS Serial Adapters", Copyright 2000 Water Pik Technologies, Inc. (2 pages).

Webpage located at, "wsiwgy://9http://www.ibuton.com/TINI/index.html." entitled, "Introducing TINI: Tiny Internet Interface", printed on Jan. 24, 2001 (2 pages).

Webpage located at, "wsiwyg://12http://www.ibutton.com/TINI/hardware/index.html." entitled, "TINI Board Schematics and Software", printed on Jan. 24, 2001 (2 pages).

Webpage located at, "wsiwyg://15http://www.ibutton.com/TINI/developers/index.html." entitled, "TINI Socket", printed on Jan. 24, 2001 (2 pages).

Webpage located at, "wsiwyg://18http://www.ibutton.com/TINI/software/index.html." entitled, "TINI Software", printed on Jan. 24, 2001 (2 pages).

Webpage located at, "www.dalsemi.com" entitled, "Dallas Semiconductor—DS2406 Dual Addressable Switch Plus 1K -Bit Memory", (30 pages).

Webpage located at, "www.dalsemi.com" entitled, "Dallas Semiconductor—DS2450 1-Wire Quad A/D Converter", (24 pages).

Clark, Tim; "Commercial and Industrial Applications of a microWebServer", presented at the 1st Annual Embedded Internet Conference held in San Jose, CA; Sep. 2001.

Gill, Philip J., "Java Makes a Splash in Real Time", Java Report Magazine, Oct. 2000.

* cited by examiner

ETHERNET

METHOD AND APPARATUS FOR REMOTELY MONITORING AND CONTROLLING A POOL OR SPA

This is based on, and incorporates by reference, U.S. provisional application Ser. No. 60/233,376, filed Sep. 18, 2000.

The present invention relates to systems, apparatus, and methods for controlling the operation of water systems, and more specifically to pools, spas, and baths.

BACKGROUND OF THE INVENTION

Systems for controlling the operation of pools and spas are well known in the art. Microprocessors are frequently used in the maintenance and control of temperature, pump operation, filter cycles, etc. Sensors are also used to monitor and regulate pH and ORP (oxidation reduction potential), particularly in pool applications. These control systems can run 24 hours a day, seven days per week, year-round, providing local control over the operational parameters of the pool or spa. Typically, these are self-contained, closed-loop systems that function autonomously, without intervention and/or control beyond the local vicinity of the physical device; i.e., no networked communication exists beyond the local surroundings.

SUMARY OF THE INVENTION

The present invention is directed to the remote monitoring and control of water parameters in various installations, and particularly water installations employing water and water control and parameter monitoring systems. One type of application installation is the pool or spa. Among other things, the invention integrates certain aspects of control technology with aspects of communications and Internet/networking technology.

In a first separate aspect of the present invention, a microprocessor-based data acquisition and control system is used to monitor the water installation, e.g., a pool or spa. The preferred system uses sensors in dynamic communication with the water in the installation (, e.g. the pool or spa water) to capture relevant data.

In a second aspect of the present invention, the first aspect is further contemplated to define specific sensors to monitor specific parameters, including but not limited to, temperature, pH, ORP, pump status, heater status, and ozone generation.

In a third aspect of the present invention, the first aspect is further contemplated to define an interface to the on-board water installation control system, e.g. a pool or spa control system. This interface would interface to the local controller via whatever means necessary to gain functionally equivalent remote control, including, but not limited to switch control interfaces, serial data interfaces, and parallel data interfaces.

In a fourth aspect of the present invention, the first aspect is further contemplated to define a network interface, enabling the data acquisition and control system to be remotely accessed.

In a fifth aspect of the present invention, the second aspect is further contemplated to define a system for storage and retrieval of the collected data.

In a sixth aspect of the present invention, the fourth and fifth aspects are further contemplated to define a method for remotely retrieving and/or viewing the collected data.

In a seventh aspect of the present invention, the third and fourth aspect are further contemplated to define a mechanism for remotely controlling the pool or spa.

In an eighth aspect of the present invention, the fourth aspect is further contemplated to define a method for automatically notifying a designated recipient of a particular error or condition, which has gone outside a specified set of parameters, and has been detected by the data acquisition system.

In a ninth system of the present invention, the eighth aspect is further contemplated to deliver the message via e-mail or pager notification to the desired recipient, and/or activate an audible alarm.

In a tenth aspect of the present invention, the second aspect is further contemplated to provide a method for calculating the proper amount of chemical additives required to achieve a desired level or balance within the pool or spa.

In an eleventh aspect of the present invention, the seventh aspect is further contemplated to provide a mechanism for using a wireless and/or cellular communications interface with a portable computer to provide portable-remote access to the pool or spa.

Other objects and advantages of the invention will be apparent from the following specification and the accompanying drawings, which are for the purpose of illustration only.

DETAILED DESCRIPTION OF THE PREFERRED EMBODIMENTS

A preferred, exemplary embodiment of the invention is described herein for a pool and/or spa installation. Although the invention is described with specificity for a pool and/or spa installation, the invention has utility for other types of water installations, including without limitation those such as cooling towers, desalination systems, aquariums, boiler feed water systems, fountains, theme-park water features, and rides.

Figure 1:
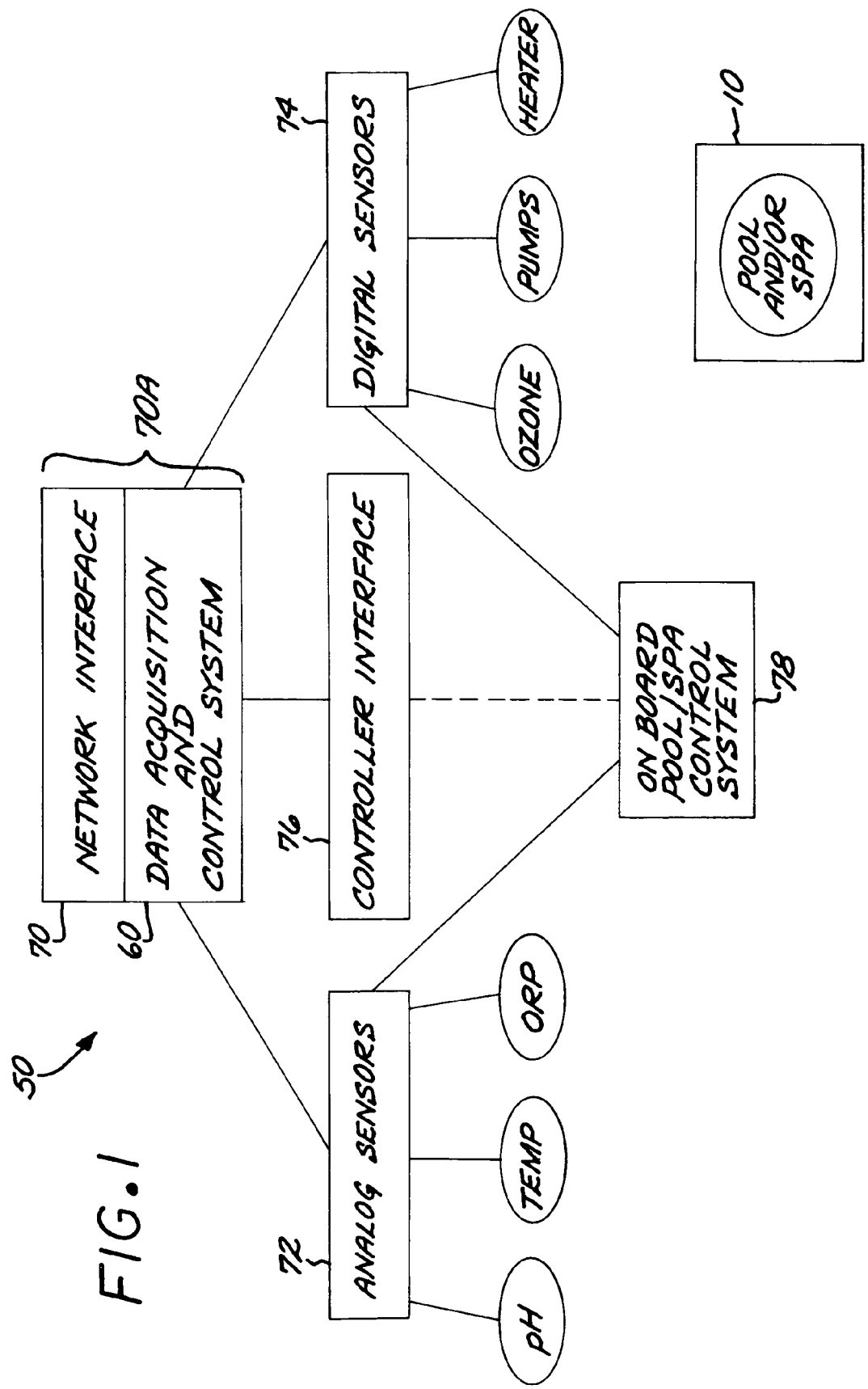
FIG. 1 is a block diagram of a preferred embodiment of the invention, illustrating a remote monitoring and control system for pools and spas.

FIG. 1 broadly illustrates a block diagram of a preferred remote monitoring and control system 50 for pool and/or spa 10. The system 50 preferably has a microprocessor-based data acquisition and control system or device 60, which is connected to a network interface 70. The data acquisition and control system or device 60 also is preferably either connected to a plurality of sensors 72, 74, which are in dynamic communication with the pool or spa 10, or otherwise in electrical communication with the on-board pool or spa control system 78. Persons of ordinary skill in the art will understand that control systems such as system 78 can control many aspects of a pool or spa, some of which require "sensors" concerning water parameters, and some of which merely "sense" the state of various pool/spa equipment (such as heater, pump, etc.). The invention has utility for both types of "sensors", as well as for combinations of them.

Among the many alternatives for such electrical communication is that illustrated by the dashed line in FIG. 1, showing that the system may also include a controller interface 76 to provide remote control and monitoring of the pool or spa controls 78.

Persons of ordinary skills in the art will understand that different sensors or multiple sensors may be used with the invention without deviating from the scope of the invention. Among other things, a wide range of combinations or selections of digital and/or analog sensors can be utilized (other than the analog sensors 72 or the digital sensors 74 of FIG. 1). In the preferred embodiment, the analog sensors 72 are interfaced to the data acquisition system through analog-to-digital converters, which convert the voltage level into digital format for processing and storage on the microprocessor-controlled system 60 and/or 78. The analog sensors 72 typically will include probes for monitoring things such as water temperature, water pH, water ORP, and water pressure, while the digital sensors 74 will allow for monitoring of things such as the status of the pool and spa systems by monitoring the pump, heater, and ozone generator status and their on-off functions. The preferred installation includes the capability of controlling a water heater and water filter associated with the pool or spa. Persons of ordinary skills in the art will also understand that other sensors and equipment (including, by way of further example and not by way of limitation, conductivity, dissolved oxygen, hardness, water clarity, bromine, copper, and chlorine) may be used without deviating from the inventive concept.

For embodiments using the controller interface 76, that interface 76 provides a direct link between the data acquisition and control system or device 60 and the pool or spa controller 78. Persons of ordinary skill in the art will understand that this interface 76 to the pool or spa control system 78 can be provided by any suitable means to allow the system or device 60 to remote control the control system 78, including, but not limited to switch interfaces, serial interfaces, and parallel interfaces—using wired and/or wireless means.

The preferred network interface 70 provides a connection point between the data acquisition and control system 60 and the outside world (that is, the world outside the conventional pool/spa control loop or system). The preferred interface 70 runs software that allows for connection through any suitable medium, including without limitation a TCP/IP (transmission control protocol/Internet protocol) stack to the Internet, a private network (any network other than the "public" Internet), or a direct interface (such as, for example, a single PC connected to the interface 70). This allows for flexibility in the type of device used to control and/or retrieve information from the device 60. Alternatively, as further discussed below, a single integrated circuit 70A may be used in place of device 60 and interface 70 to achieve the same result.

The preferred system 60 also includes hardware and software for storing data collected from a selected (or selectable) preceding time interval (such as the previous 24 hours). Preferably, the system 60 also permits selectable control of the sampling interval (hourly, every 5 minutes, on demand, etc.) for each of the control parameters (temperature, etc.). Again preferably, this collected information can be retrieved via the network interface, locally or remotely. The data can be presented in a variety of formats, including on-line graphs, charts, or tabular format, and through, for example, means indicated at the website: http://wwwjava-.sun.com/ (which are incorporated herein by reference). FIGS. 6A-6D illustrate exemplary browser screens providing data showing status of various spa parameters and control functions, depicting some of the many ways in which various data can be presented.

In the preferred embodiment, a remote server 100 (FIG. 2) is used to collect and maintain data for periods greater than for which the data is stored in system 60 (i.e., if the "local" data storage period is the preceding 24 hours, data previous to that 24 hours is stored on remote server 100). The server 100 collects the information from the data acquisition and control system 60 (or alternatively device 70A (discussed further below), which implements the functions of both the data acquisition and control system 60 and the network interface 70) at an appropriate and/or selectable interval (such as daily), storing the files in appropriate locations for future retrieval.

As further discussed below, the preferred data acquisition and control system 60 and the remote server 100 also include software algorithms for detecting a particular error condition or status, and then alerting a desired recipient via e-mail, direct pager contact or other communication method, and/or activating an audible alarm. Exemplary error conditions or status data include high water temperature (e.g., over 109° F), pH/ORP out of bounds, an open spa cover or pool gate, and that the pool/spa pumps are thermally cycling (running to motor overheat). Among other things, the e-mail message can be a textual e-mail notification to the user's e-mail address. Alternatively or in addition, a direct pager message can be sent by the system (via software, hardware, or a combination of the two) direct dialing the user's pager number, such as from the system 60 or from the server 100. Preferably, server 100 monitors incoming data from system 60. When a preselected error condition is detected, an alert is triggered, causing the server 100 to take the desired action, such as sending an e-mail, sending a pager message, etc. Persons of ordinary skill in the art will understand that, for such dialing or other communications, conventional safeguards such as error codes can be utilized.

The system preferably may also use the various sensors (such as pH, –ORP, and water clarity sensors) to monitor the water chemistry, providing a means to calculate the required chemical additives necessary to achieve the desired water balance. By way of example, if the volume of the water in the system is known or monitored and the strength or other nature of the additive is known, a desired concentration of the additive can be achieved by controlling the amount added at any given time. Among other things, this information can even be forwarded through the remote server 100 to a specific chemical supplier or pool/spa maintenance service, or to the homeowner via data transmission, e.g., via e-mail, pager or other connection method. Based on that communication, the homeowner or service can add further chemicals as needed/desired. For systems permitting "automatic" chemical treatment, those automated aspects of the system can be coordinated with the other control features of the invention to permit "remote" addition of chemicals, etc. Thus, similar to the data acquisition and control device, the preferred remote server also includes software algorithms for detecting a particular error condition and status condition.

Figure 2:
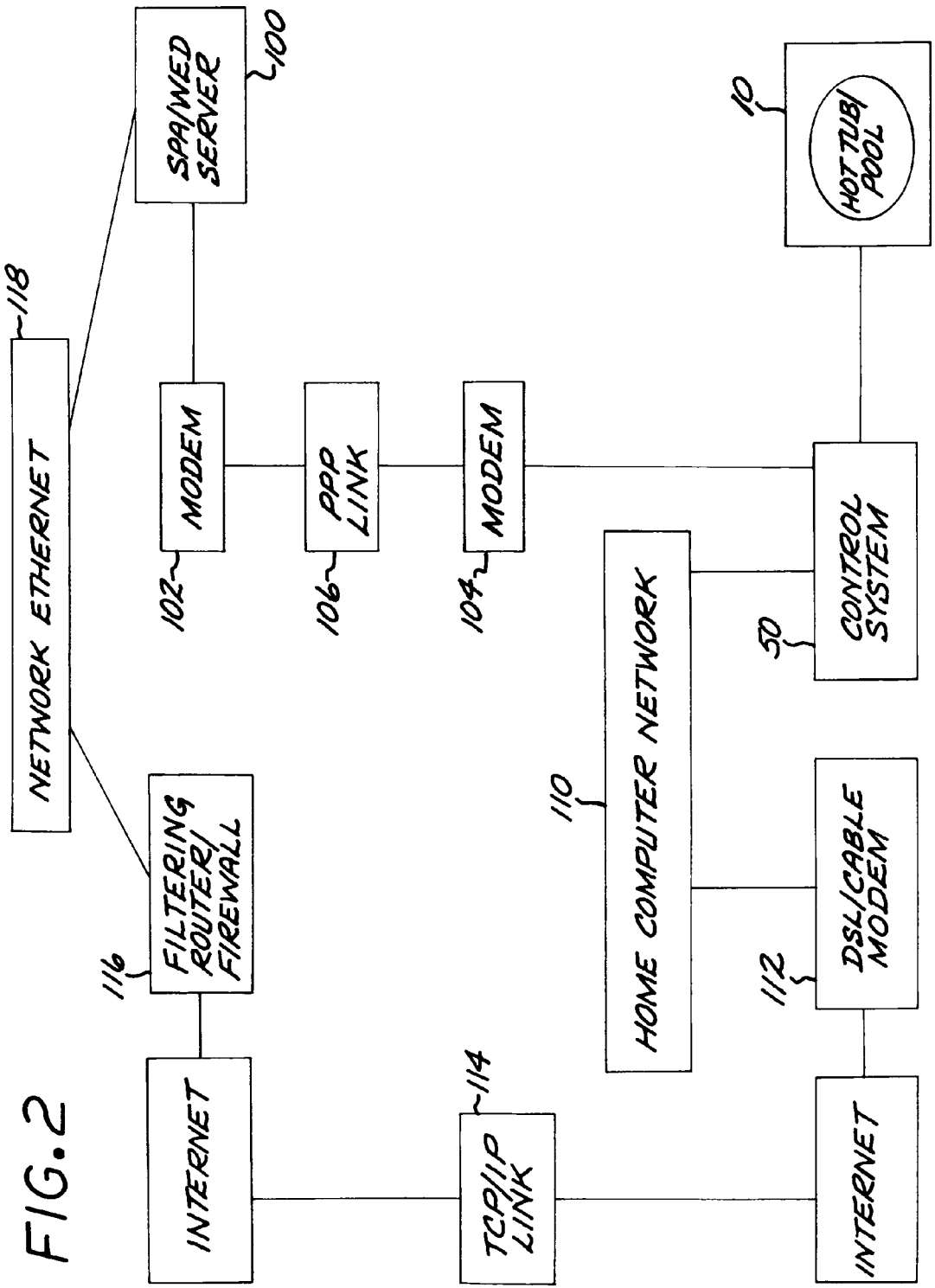
FIG. 2 is a block diagram illustrating an exemplary network architecture for the system of FIG. 1.

FIG. 2 is a schematic block diagram of an exemplary network architecture permitting remote monitoring and control of the pool/spa 10. This diagram illustrates exemplary connection details of a network architecture used to communicate between various components, including the remote server 100 (here labeled a Spa-Web server) and the remote monitoring and control system 50. Among other things, FIG. 2 illustrates both high-speed home-Internet connections (using in this example a DSL or cable modem generally indicated as 112), and a dial-up connection through a traditional telephone service using an analog modem 104. However, persons of ordinary skill in the art will understand that any suitable network connection and communication means may be utilized.

In the case of the dial-up connection, the system 50 preferably communicates through the modem 104 via a Point-to-Point Protocol (PPP) link 106 and analog modem 102 to the Spa-Web server 100. In the case of high speed connections, the system 50 preferably communicates through a home computer network or LAN 110 with the DSL/cable modem 112 and via the Internet through a Transport Control Protocol/Internet Protocol (TCP/IP) link 114, through a filtering router/firewall 116 to a network ethernet connection 118 and then to the Spa-Web server 100.

Persons of ordinary skill in the art will also understand that, in any particular implementation for a given pool/spa, the connection to the server 100 may be only through a dial-up connection, or only through a high-speed connection; or through some other suitable means or combinations of communication technologies. FIG. 2 simply shows different illustrative techniques for making the connection to the server 100. By way of further example, the connection between the system 50 and the home network 110 can be a hard-wired connection, or a wireless connection, e.g. a "BlueTooth" data transmission link. Such wireless technology can be used in many areas of the invention, such as providing a mechanism for using a wireless and/or cellular communications interface with a portable computer to provide portable-remote access to the pool or spa. Embodiments in which the data acquisition and control system or device 60 is in electrical communication with the onboard pool or spa control system 78 (such illustrated by the dashed line in FIG. 1) include embodiments in which the TINI chip (see below) is mounted onto the conventional pool/spa controller board. In such embodiments, the TINI chip can communicate wirelessly to a network interface/server 70, so that the bulk of the webpage communication and processing occurs on that server rather than on the TINI itself.

In FIG. 2, the data acquisition and control system 60 and the network interface 70 preferably are provided in an integrated circuit (IC) device 70A (FIG. 1). One of many such suitable devices is presently available under the name "TINI Network Interface", and is commercially available under part number DSTINI1-1MG, Dallas Semiconductor, Dallas Tex. This device preferably performs several functions including data collection.

Figure 3A:
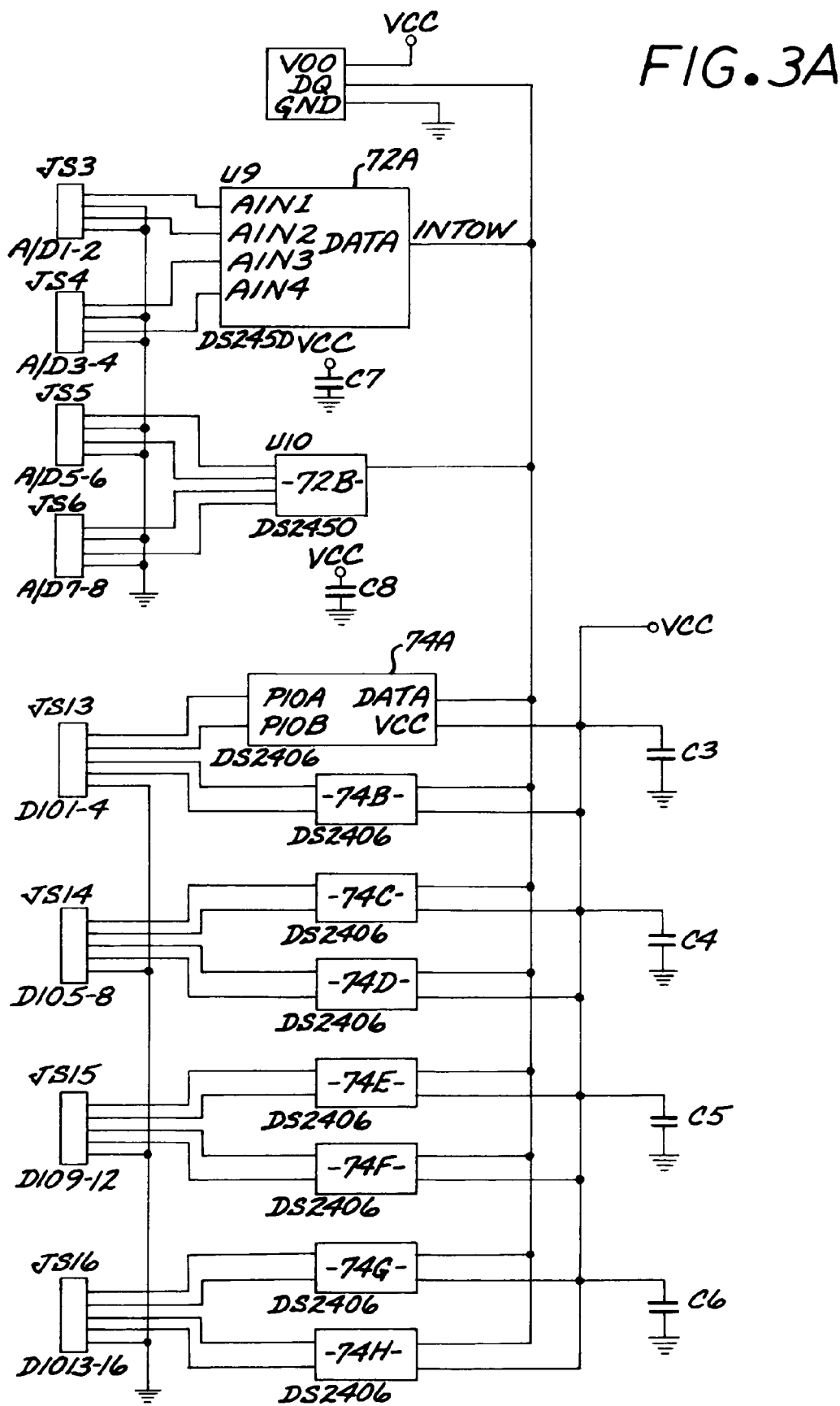
FIGS. 3A-3D are schematic diagrams illustrating certain aspects of an exemplary embodiment of the system of FIG. 1.
Figure 3B:
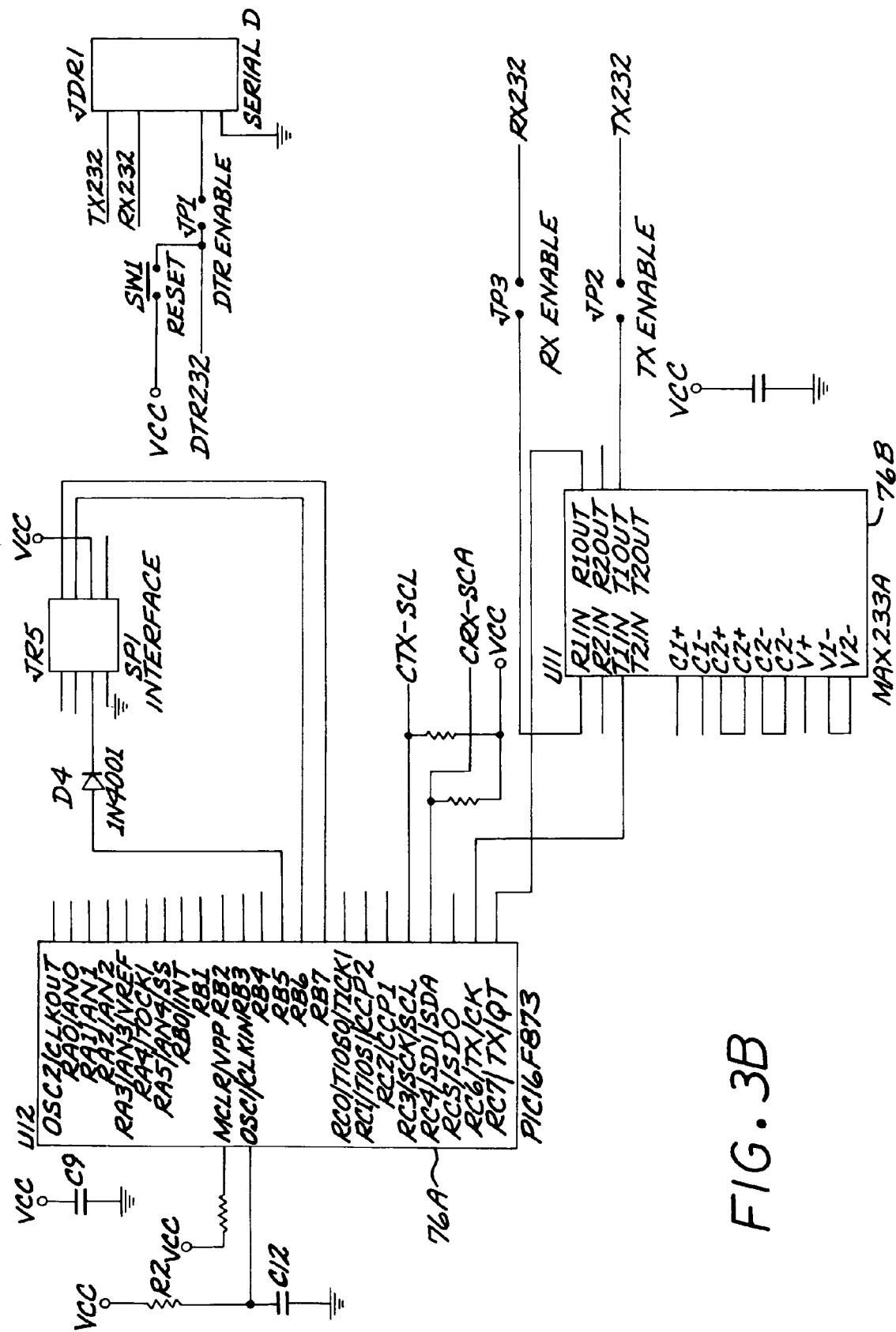

Details of preferred device 70A and its related components are described in FIGS. 3A-D and elsewhere herein. Persons of ordinary skill in the art will understand that any suitable circuitry or other controls and communication technology may be effectively utilized to practice the invention. FIG. 3A is a schematic diagram illustrating an exemplary embodiment of aspects of the system of FIG. 1. ICs 72A, 72B are digital-to-analog converter devices which implement the analog sensor 72. A device suitable for the purpose is the quad A/D converter device, model DS2450, marketed by Dallas Semiconductor, Dallas, Tex. ICs 74A-74H are addressable switch devices which implement the digital sensor 74. A device suitable for the purpose is the dual addressable switch with 1 K-bit of memory, model DS2406, marketed by Dallas Semiconductor. Devices 76A-76B (FIG. 3B) implement the pool/spa controller interface 76. Device 76A is a microprocessor, e.g. a PIC 16F873 device. Device 76B is a MAX 233 RS 232 level translator device. Device 70A is the TINI Network Interface device, in this exemplary embodiment a Dallas Semiconductor part number DSTINI1-1MG.

Figure 3C:
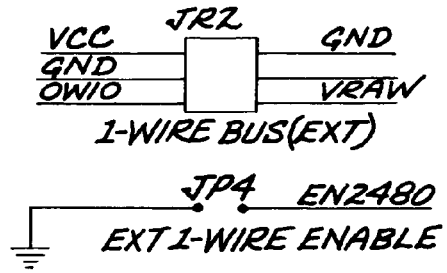
Figure 3C:
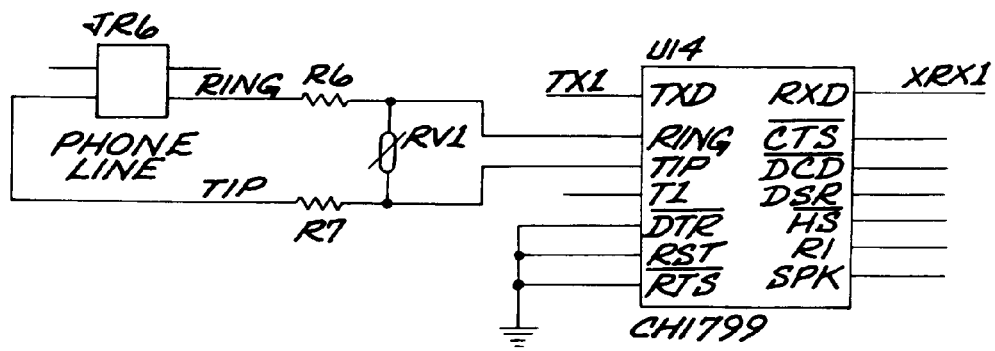
Figure 3C:
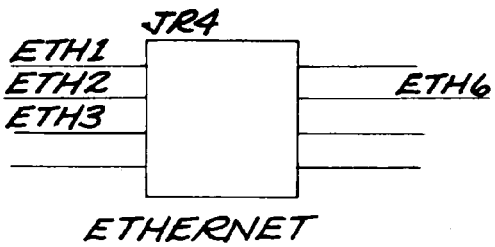
Figure 3C:
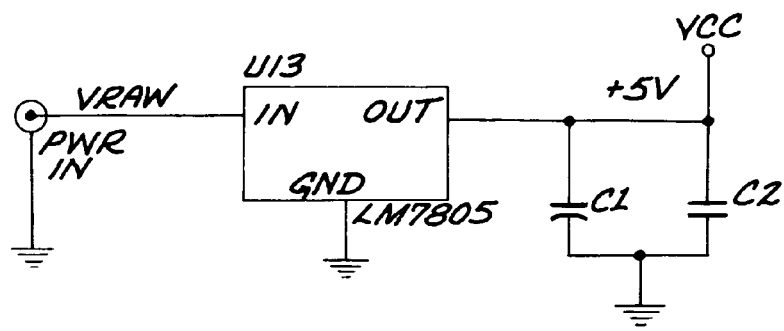
Figure 3D:
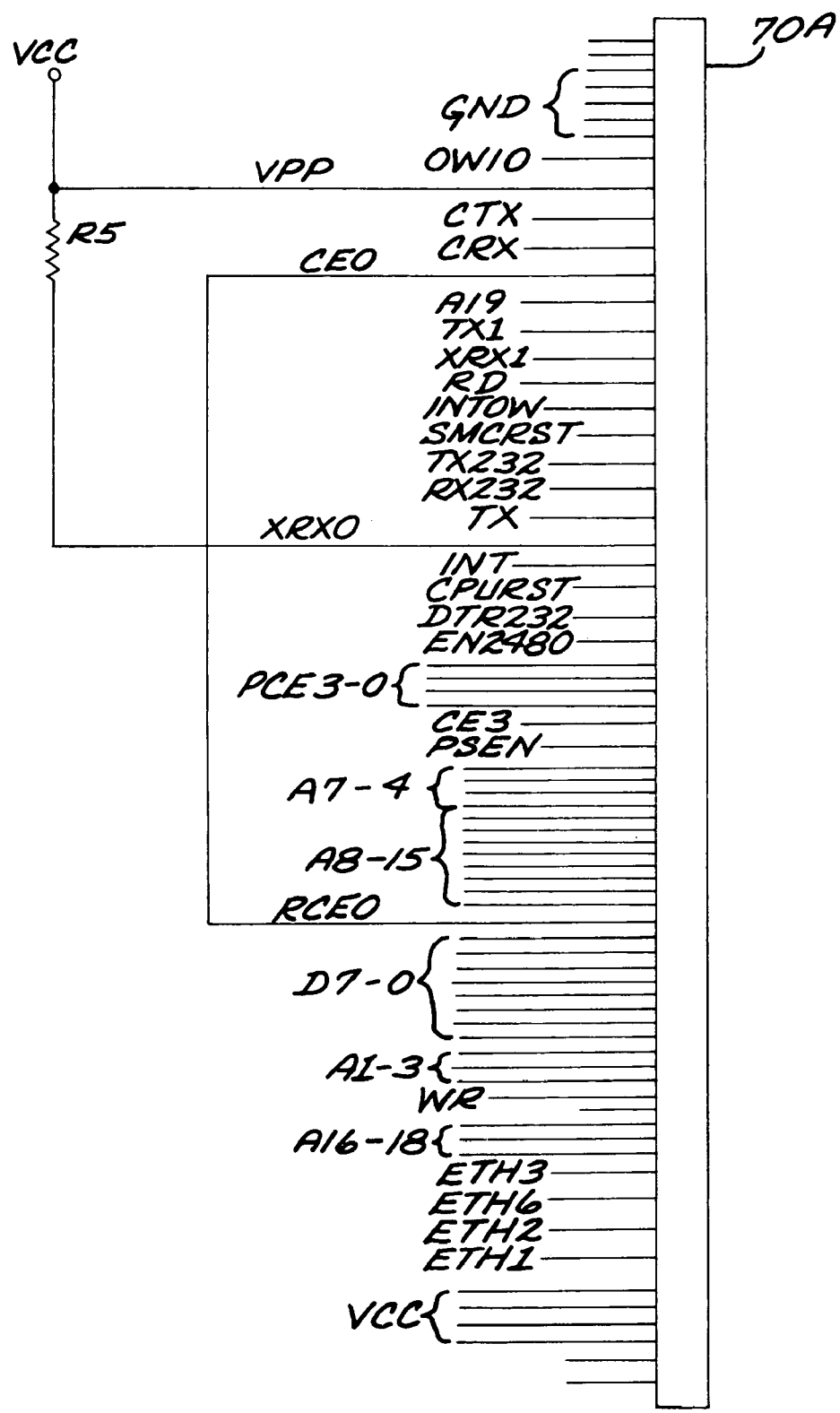

As illustrated in FIGS. 3C and 3D, device U14 preferably implements the modem 104 function. Among the many suitable devices that can be utilized is the commercially available Cermetek Model 1799 33.6 kbps embedded analog modem. It implements any and all dial-out connections (PPP connections to the Internet or directly to Server 100), as well as any system 50 direct paging.

Connector JR4 shown in FIG. 3c is preferably used to connect system 50 to a high-speed Internet connection, including but not limited to a cable or DSL modem, and/or a local network.

Figure 4A:
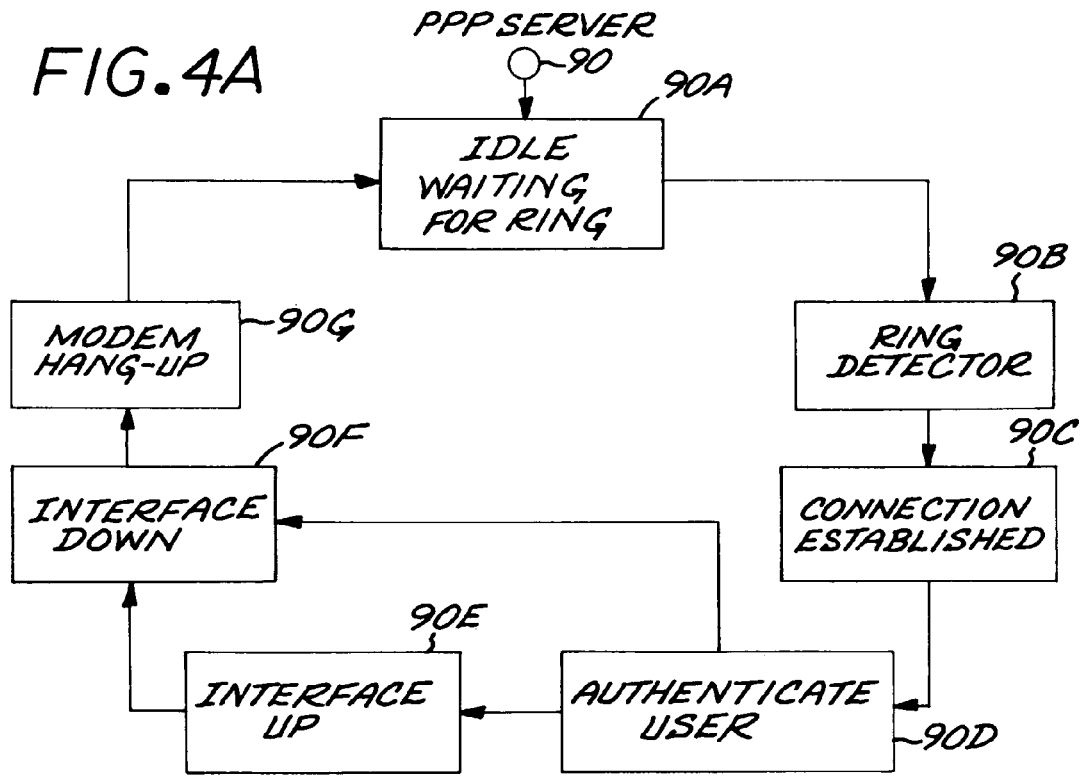
FIGS. 4A-4B are state diagrams illustrating the operation of the respective exemplary server functions performed on the network interface of the system of FIG. 1.
Figure 4B:
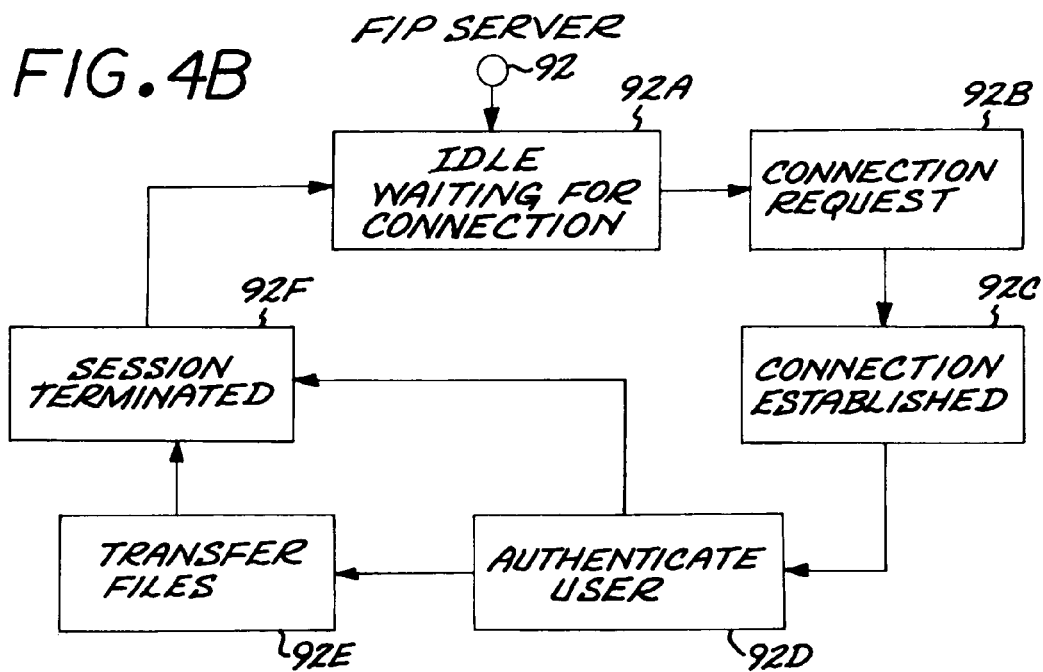

FIGS. 4A-4B are state diagrams which illustrate the preferred operation of the respective exemplary server functions performed by the network interface 70. The Point-to-Point Protocol (PPP) server software 90, whose function preferably can be implemented by the network interface 70 (i.e., software incorporated into the network interface 70), acts to accept incoming dial-in connections through the telephone modem 104. Once the connection is established, as illustrated in FIG. 4A, the remote server preferably has an "Internet" link into the system 50. As will be appreciated by persons of ordinary skill in the art, the remote server preferably links by any suitable means. In FIG. 4B, the File Transfer Protocol (FTP) server 92, whose function can also be implemented by the network interface 70, accepts requests for the transfer in/out of specified files which reside on the system 50.

In the preferred state diagram of FIG. 4A, the idle state 90A indicates the state in which the PPP server software 90 (preferably on board the IC 70 or 70A, although it can be provided in the form of a separate element or circuit) is waiting for a ring indication from the modem 104. Once the ring is detected at state 90B, the call preferably is answered by the modem 104. At 90C, the connection is established, and initial LCP (line control protocol)""negotiation occurs between the PPP server on device 70 and the server 100. At step 90D, the server 100 preferably requires a username/password in order to log into the server. Persons of ordinary skill in the art will understand that, in certain unsecured applications, the username/password requirements could be omitted, and that the roles of the PPP connection (including password protections, etc.) are reversible, i.e., with the server 100 acting as the PPP server, accepting connections from numerous devices 70A.

In the preferred system, after the user has been authenticated, at 90E, the PPP connection is established, allowing TCP/IP traffic to flow across the telephone interface. State 90F is the "interface down" state in which the PPP connection is closed, shutting down all TCP/IP connections. At state 90G, the modem 104 is commanded to hang-up the telephone line. If instead the server cannot authenticate the user, the PPP connection is immediately terminated.

Referring now to FIG. 4B, in the preferred embodiment, state 92A is an idle state, with the FTP server 92 waiting for a TCP/IP connection from the network interface 70. At state 92B, a connection request is made, and received, and a TCP/IP connection is opened through the network interface 70. At state 92C, the connection is established with the requester through the network interface 70. State 92D is a user authentication state, with the FTP server requesting the user name and password for authentication. At state 92E, the authenticated user is allowed to transfer files from device 60. State 92F indicates the termination of the session, with the FTP session closed and the TCP/IP connection brought down. If the FTP server instead cannot authenticate the user, the FTP session is immediately closed.

Figure 5A:
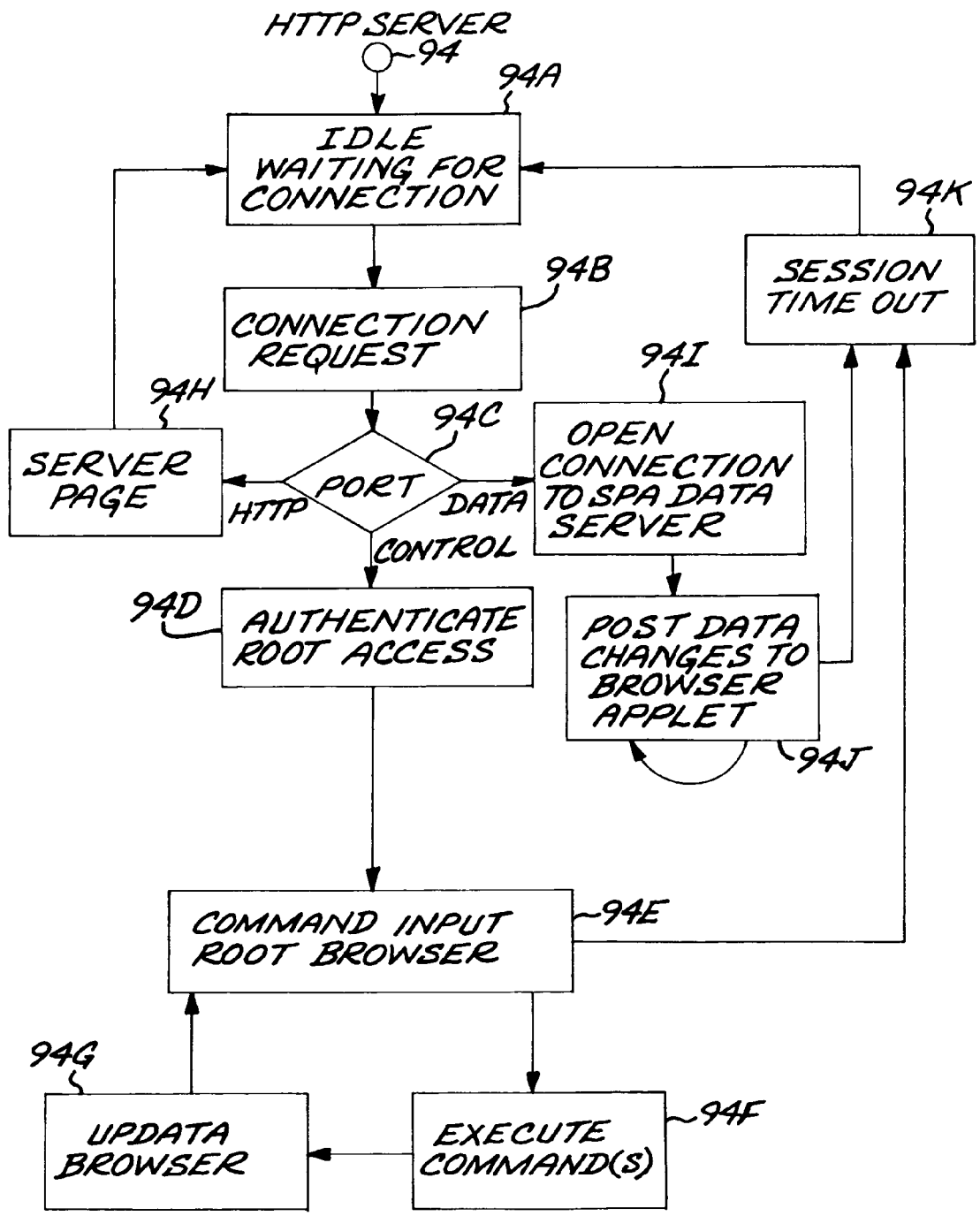
FIGS. 5A-5B are state diagrams depicting operation of exemplary functions performed on the network interface of the system of FIG. 1.

FIG. 5A is a state diagram depicting operation of exemplary functions preferably performed on either network interface 70 or server 100. In the preferred system, a Hypertext Transport Protocol (HTTP) server 94 accepts requests from Internet browsers (i.e. the remote peers) which are connected to the network interface 70. Depending on the type of request (e.g. WebPage, Data or Control), the server 94 routes the request to an appropriate function to process the data/request. Preferably, the Spa Data Server 94I illustrated in FIG. 5A is also preferably implemented on the network interface 70, but could also be implemented on network server 100.

For the state diagram of FIG. 5A, state 94A is an idle state, wherein the HTTP (web) server 100 is waiting for a connection request on TCP port XX, where XX may be used to specify an HTTP Port which server 100 (or network interface 70) listens for each system 50 (see further discussion regarding 94C, where the selection of Port XX is made). The port will be one of: HTTP, Control, or Data, where Control and Data are uniquely assigned for each system 50 installation. State 94B is a connection request state, wherein the HTTP server has received a TCP connection request on port XX. State 94C is a conditional state, wherein operation jumps to the appropriate state based on which port is requested (HTTP, Control, Data). If the request is on the Control port, operation branches to Authenticate Root Access state 94D. Here the user is required to authenticate (with a password) for root level access. Upon successful authentication, a control session is opened. At state 94E, the control session accepts commands from the user's browser, thus limiting the ability to make changes to the listed commands. Although persons of ordinary skill in the art will understand that a variety of commands and combinations thereof may be provided on the menu, the preferred system includes, by way of example, commands such as changing SetTemp, adjusting Filter Times, turning Pumps ON/OFF, switching modes, etc. Preferably, commands other than those in the menu are not recognized or processed by the system. At state 94F, the HTTP server causes the desired command to be executed on device 60. The HTTP server sends out any new or changed information to the user's browser at state 94G.

In the preferred embodiment, if the request (state 94C) is on the HTTP port, operation jumps from the Port 94C to the Server Page state 94H. In the case of a "plain-text" HTTP/HTML request (as compared to graphical or other more complicated content)"", the server merely transfers the specified HTML page to the user's browser, operating as a typical web server. If the request is on the data port state 94C, operation jumps to the Open Connection to Spa Data Server state 94I, to open a connection to the spa data server. In this case, a data port connection must be established with the spa data server to acquire dynamic information about the spa (e.g., temperature, pH, ORP, etc.). At the Post Data Changes to Browser Applet state 94J, the information displayed in the user's web browser is dynamically updated in real-time using a Java applet. The session preferably is then terminated at state 94K, after a selected period (such as a period of no less than 30 seconds) of inactivity (due to the browser being closed, the link broken, or other reasons).

Figure 5B:
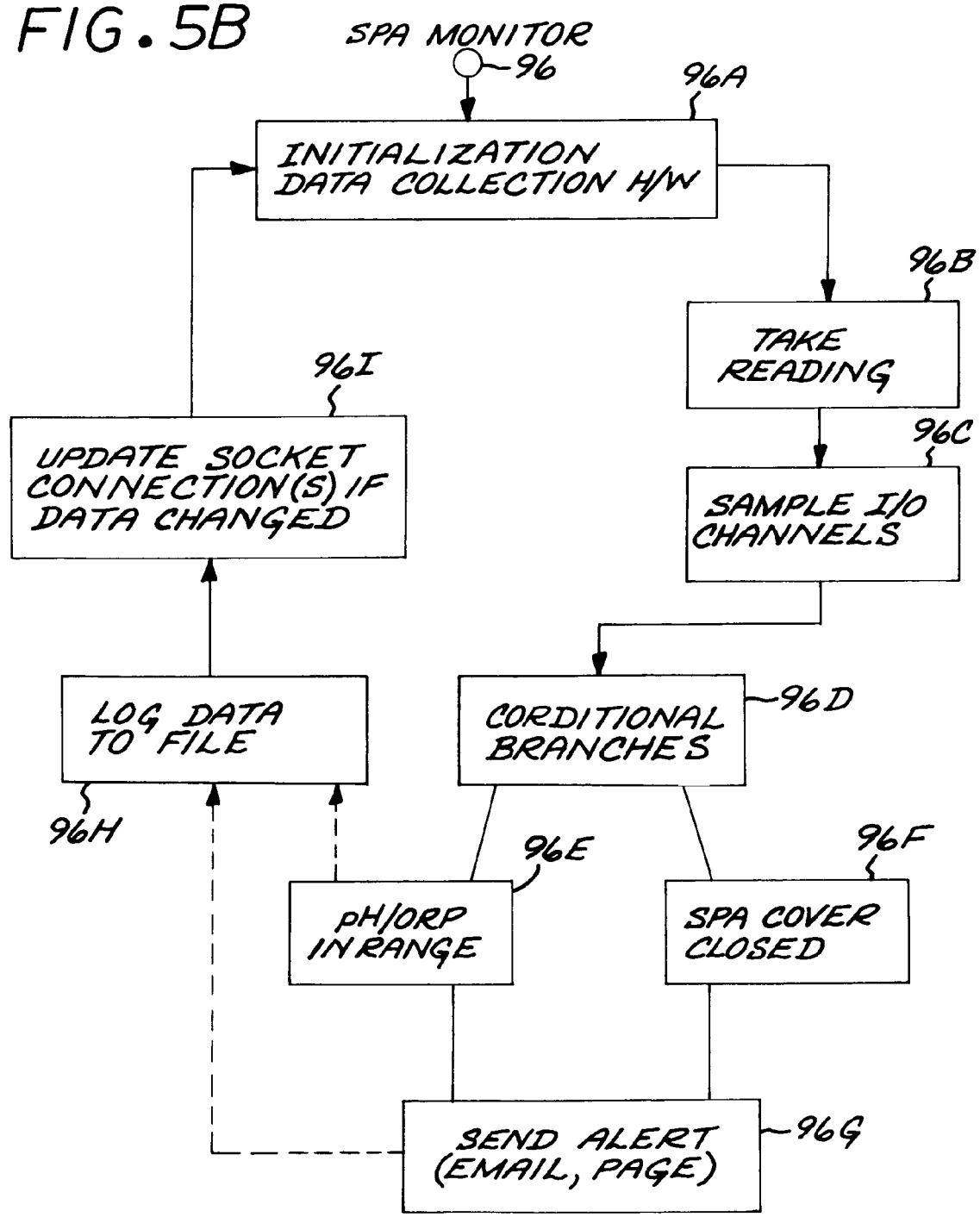

FIG. 5B is a state diagram depicting preferred operation of exemplary functions performed by the data acquisition and control system 60. Among other things, FIG. 5B illustrates the preferred operation of the spa monitoring program 96, which is a data collection and logging program that executes in the background of the system 50. The Spa Monitoring program 96 continuously takes readings, samples the I/O channels, logs the data to a data file, and updates any open Internet browsers with the new data. State 96A represents a preferred initialization state, which is responsible for the initialization and setup of all hardware (device 60) used in the data collection process. At state 96B, the software purges the previous reading and prepares to take a new "snapshot" of all monitored points. At state 96C, the software executes commands which cause the appropriate hardware devices to sample all the connected monitor points, (e.g., both the analog and digital sensors can be commanded to take readings). State 96D is a conditional state, wherein (if configured) the software compares selected monitored values to preset limits and causes a desired action to occur. Two examples of monitored values are illustrated in FIG. 5B, shown as states 96E, 96F. State 96E is a state to determine whether the water pH and ORP are within preset limits. If these parameters are within range, the software continues to check all other conditions, i.e. all other monitored values before transitioning to state 96H. Otherwise, if the parameters are not within limits, operation jumps to state 96G, and an alert is communicated, e.g. an e-mail or pager message to the user, or service personnel.

State 96F is another conditional branch example, which is triggered by the opening of the spa cover. Here again, if the cover is open, then operation branches to step 96G to send an alert; otherwise, operation proceeds to state 96H or to other conditional branches.

State 96H is a state wherein all monitored channels are written to a file on local storage for later transfer to an off-site server (such as server 100). State 96I is a state to update the socket connection(s). Here, if a state or value has changed on a monitored channel, the new information is sent out through the selected TCP socket.

Figure 6A:
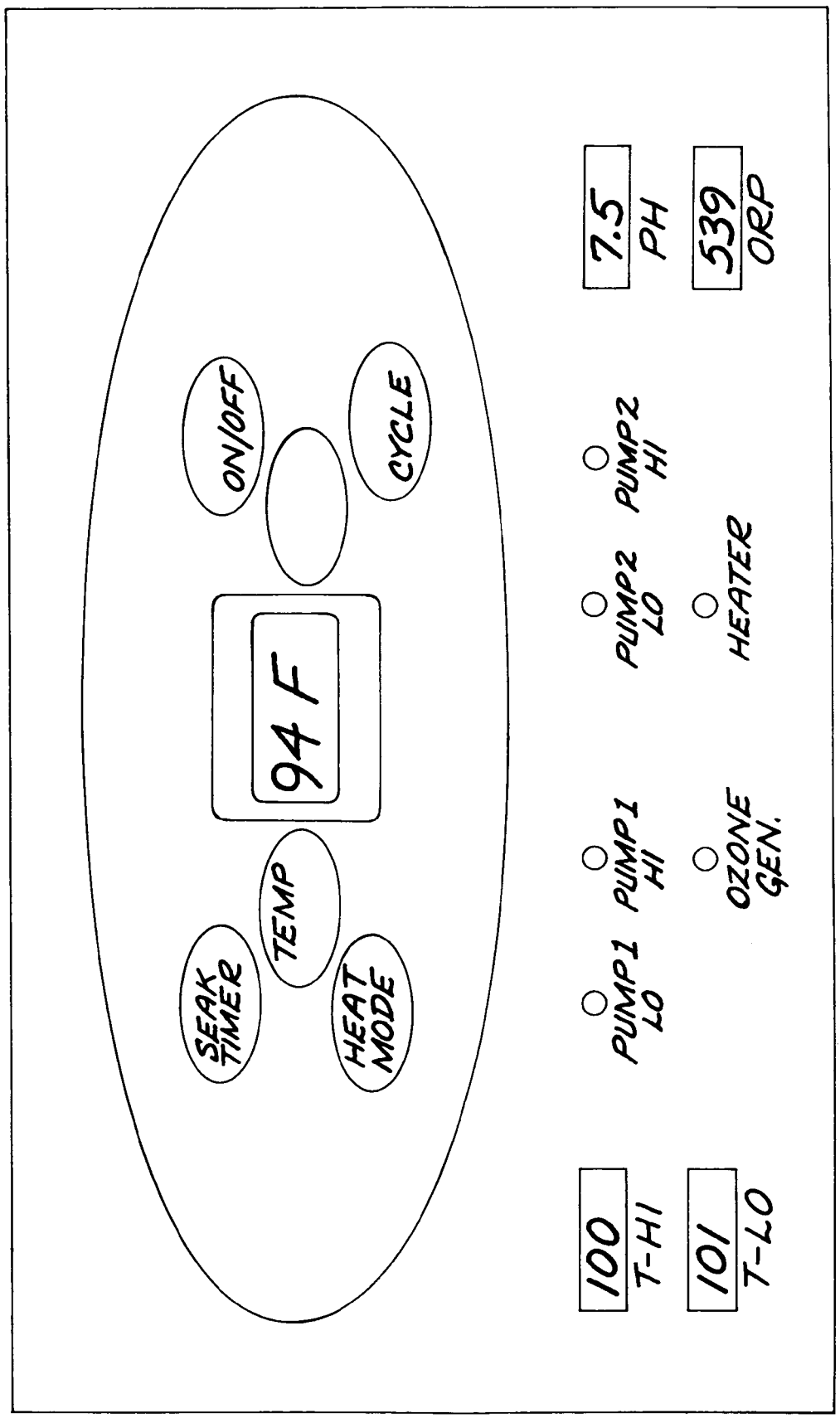
FIGS. 6A-6D illustrate exemplary browser screens providing data showing the status of various spa parameters and control functions, and depicting some of the many ways in which the data can be presented.

Persons of ordinary skill in the art will understand that the data from the system can be presented and used in a wide variety of formats, layouts, etc. Among the many variations are the examples set forth in FIGS. 6A-6D, which illustrate exemplary browser screens. In FIG. 6A, for example, a browser screen can display current readings in the lower boxes (high and low temperature settings on the left, and PH and ORP on the right), and the status of various equipment (pumps, ozone generator, heater, etc.) can be displayed in the middle lower portion of the screen (in the example of FIG. 6A, the circle adjacent each piece of label toggles on or off as an indicator). Various spa parameters and control functions can be readily accessed by clicking on the icons in the upper half of the window, to open other detailed forms/windows for additional information and/or control transmissions.

Figure 6B:
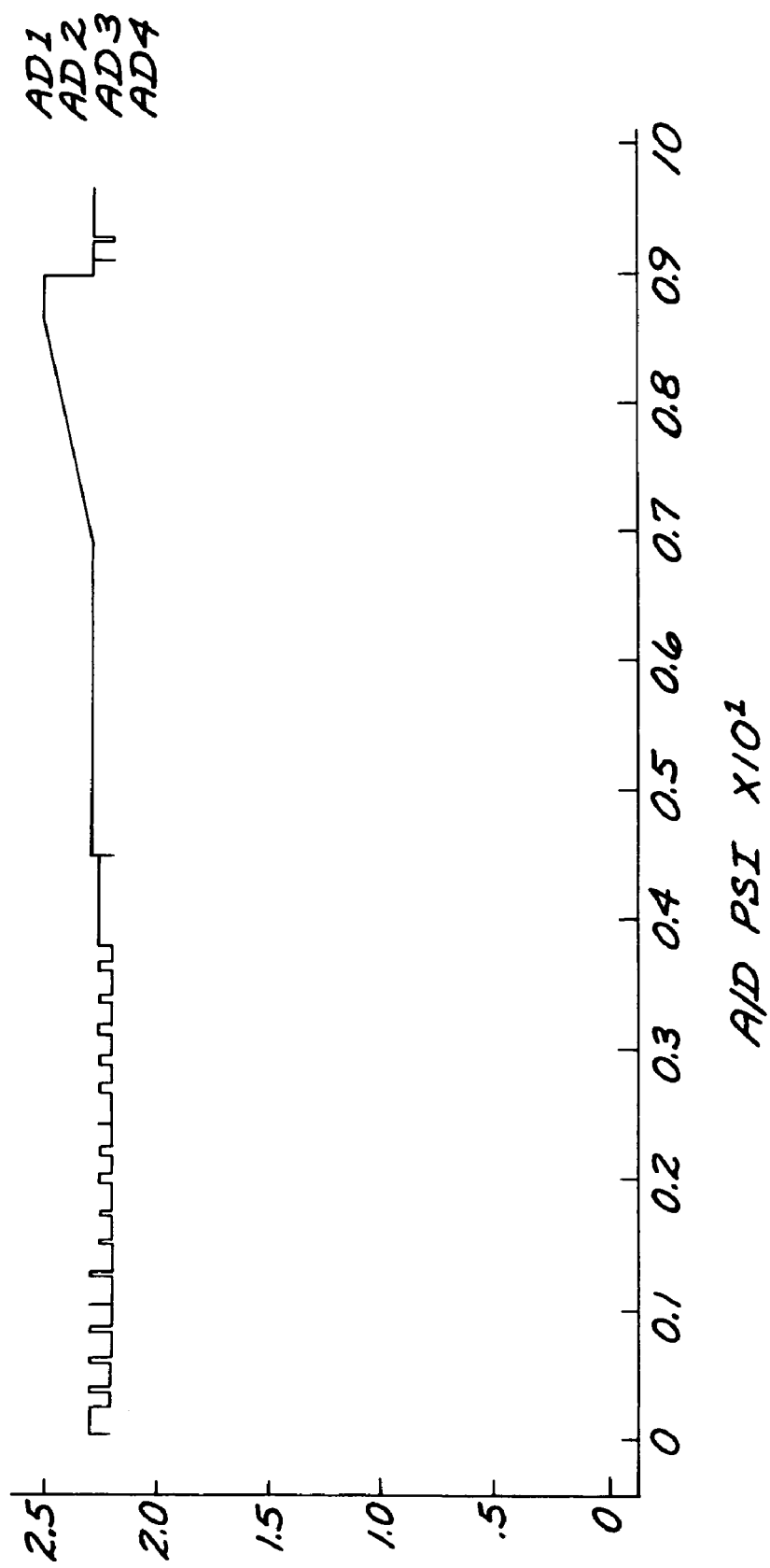
Figure 6C:
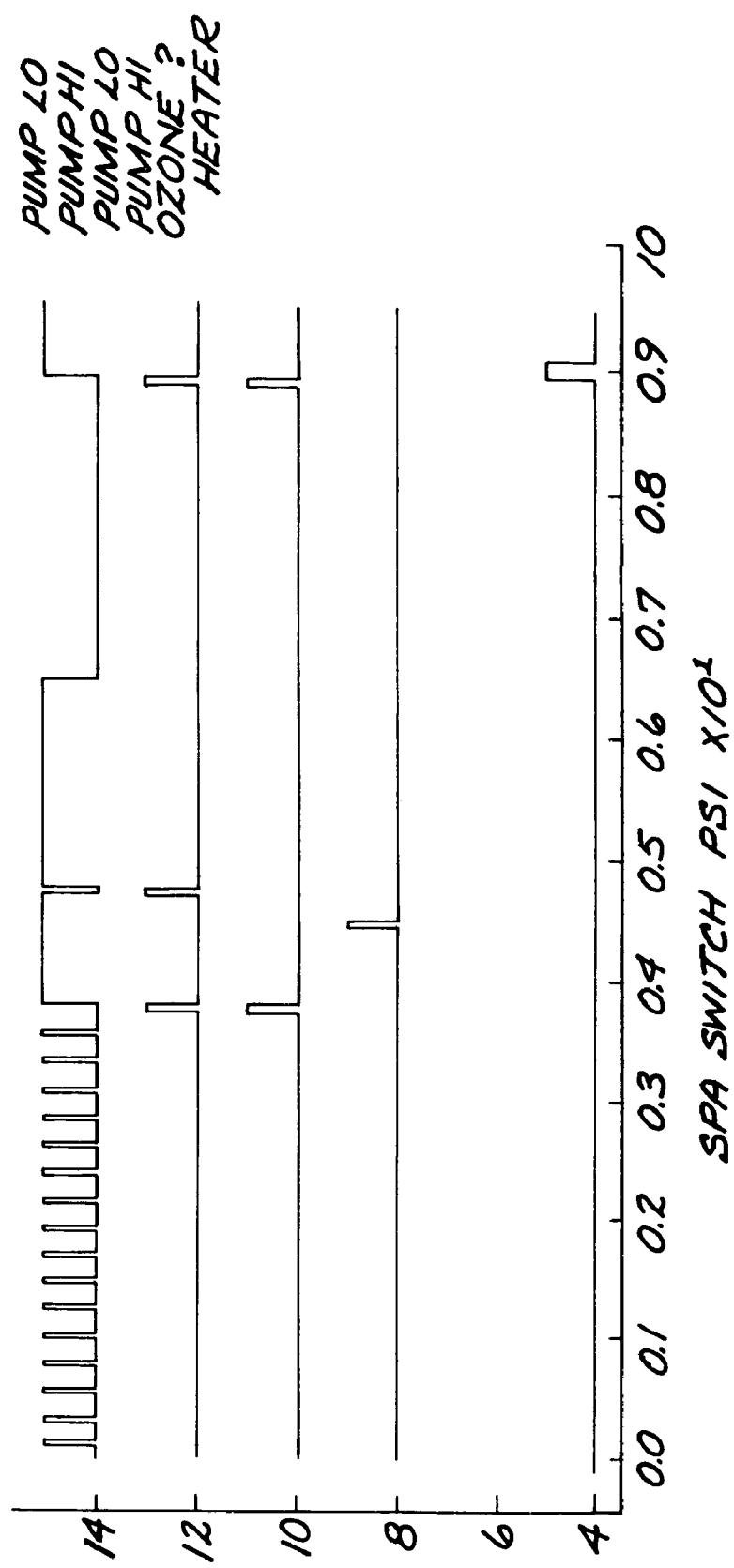
Figure 6D:
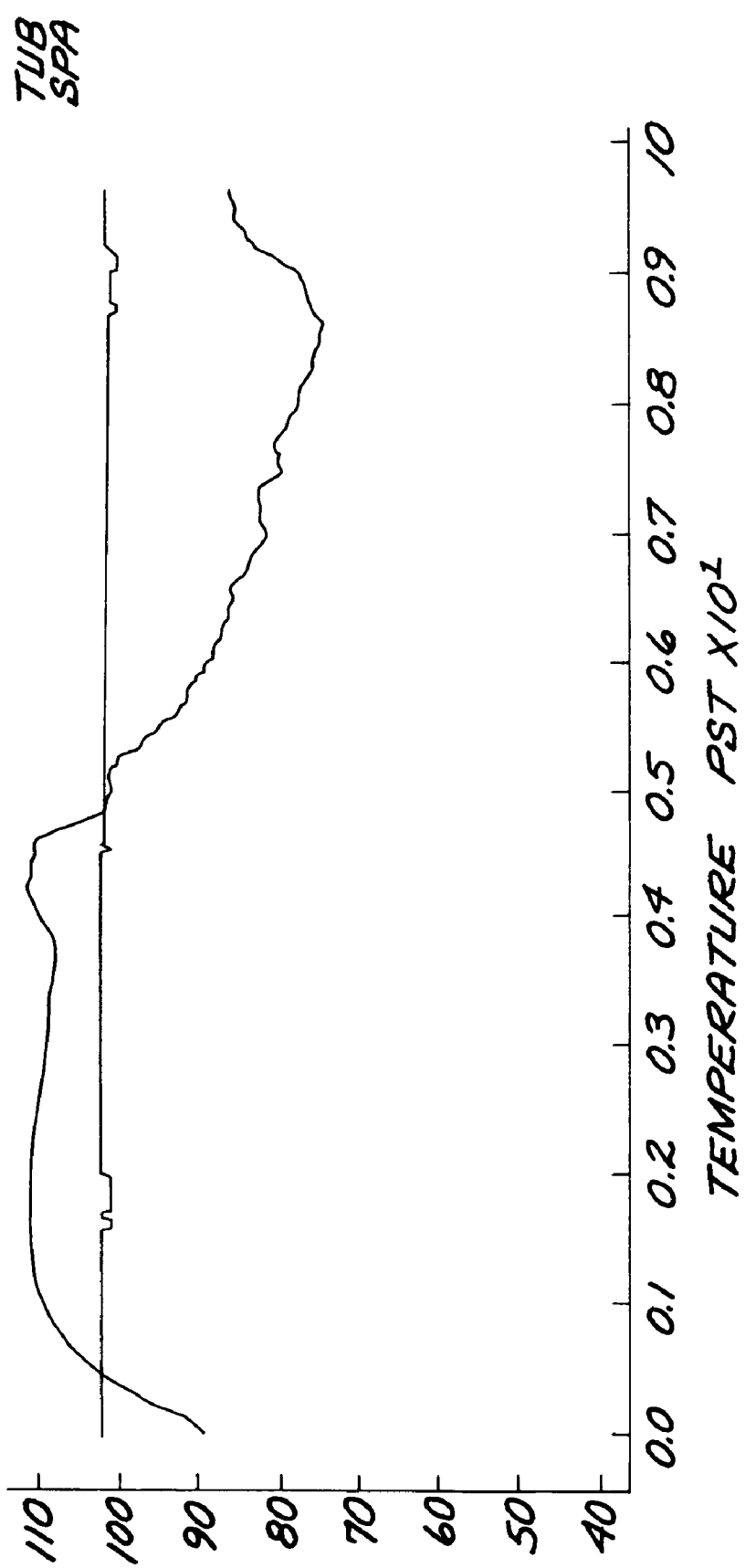

FIGS. 6B-D illustrate some of the many other ways that data regarding the spa/pool can be displayed to a user, including the history of certain parameters over the course of time. Persons of ordinary skill in the art will understand that there are many ways to display and utilize the data gathered by the invention.

Figure 7A:
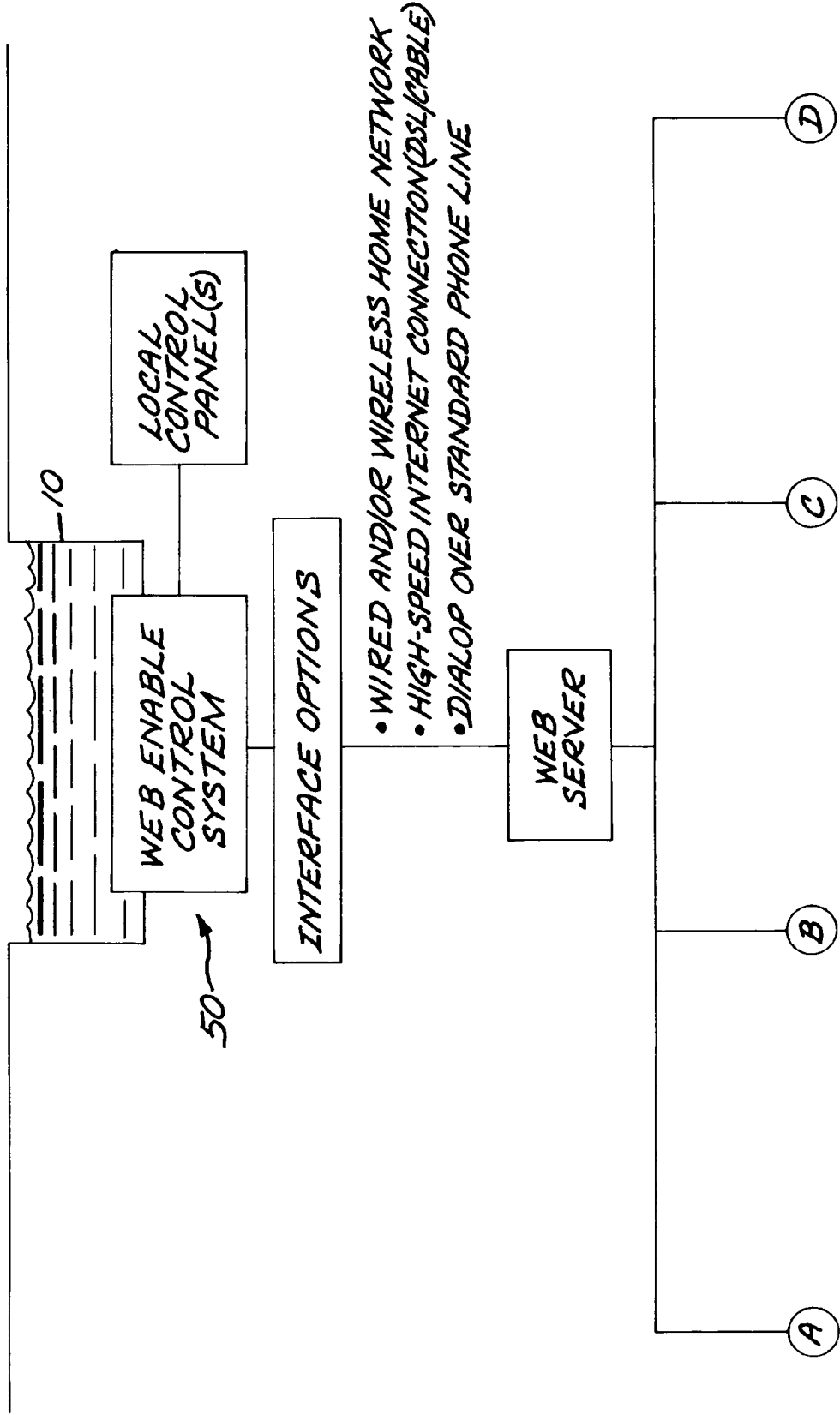
FIGS. 7A-7C collectively are a functional network block diagram illustrating exemplary applications for the system illustrated in FIGS. 1-6.

FIG. 7A is a functional network block diagram illustrating preferred exemplary applications for the system 50. Persons of ordinary skill in the art will understand that elements A-D at the bottom of FIG. 7A indicate a connection to the corresponding elements A-D on the tops of FIGS. 7B and 7C.

Figure 7B:
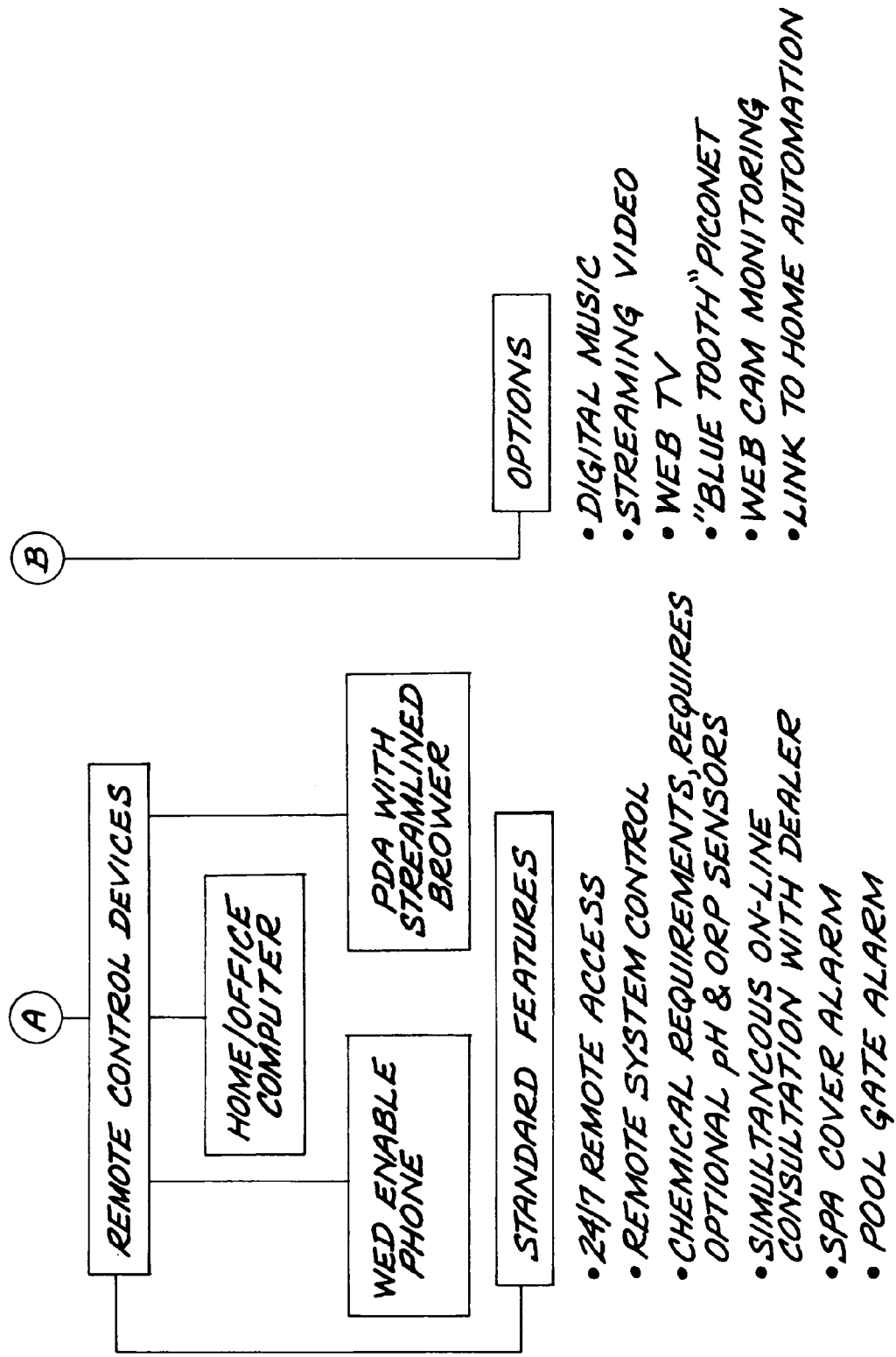
Figure 7C:
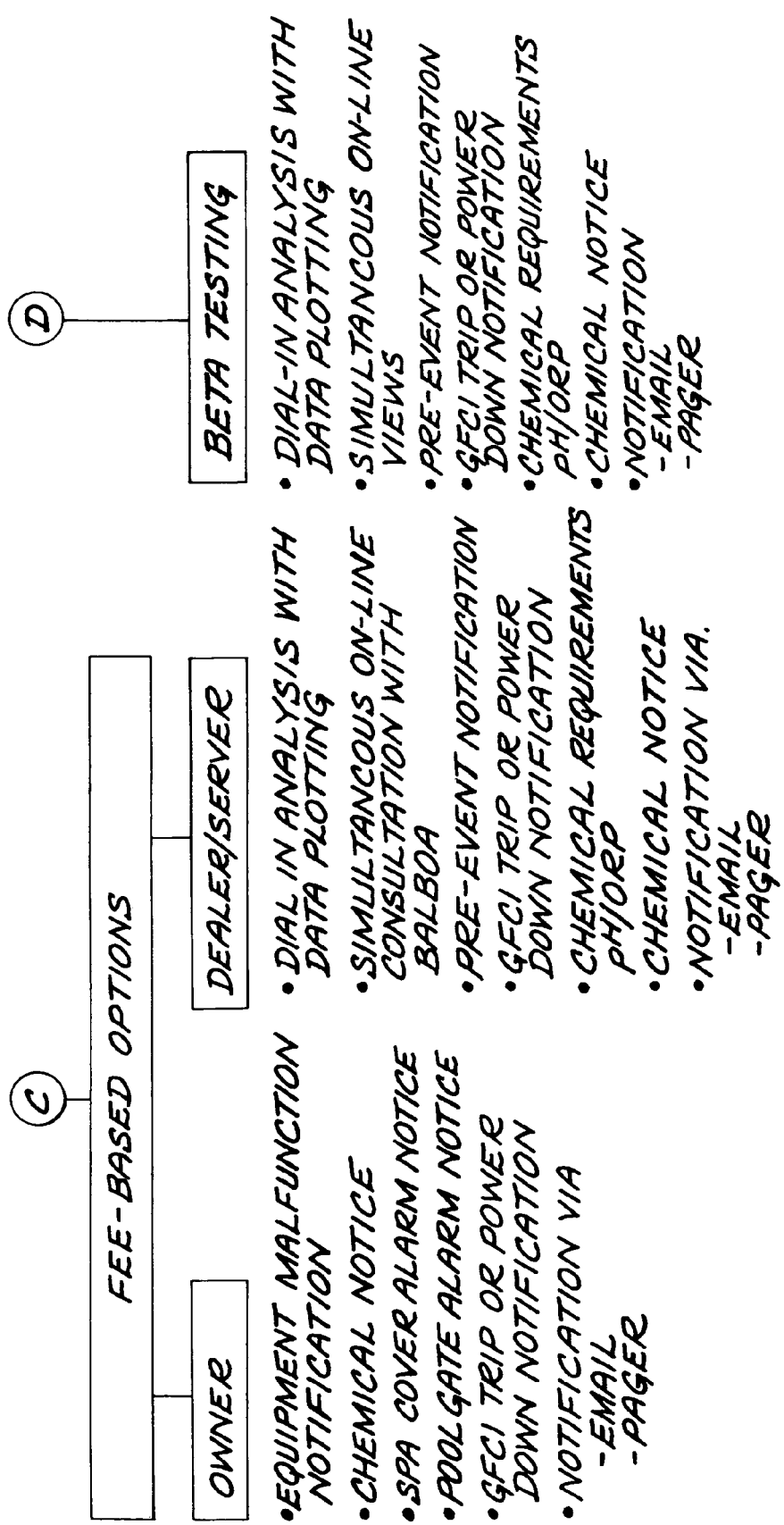

As shown in those FIGS. 7A-C, the system 50 preferably can be accessed through the remote server by a wide range of remote control devices. These include, by way of example and not by way of limitation, a web-enabled phone, a home/office computer, or a PDA with a streamlined browser. These and other user access devices/interfaces can perform remote access function, determine chemical conditions in the water with pH or ORP sensors, conduct simultaneous on-line consultations with others including a chemical dealer or maintenance personnel, or receive alarms that the spa cover or pool gate is open.

A wide variety of other functions can be monitored and controlled, such as transmitting digital or other music, streaming video, or Web TV via the server 100 to a pool/spa sound/entertainment system. Similarly, the system can be used for remote Web cam monitoring of the pool/spa premises (FIG. 7B). Links to home automation systems can also be provided.

Other features, typically fee-based services, preferably can provide various notices to the user, and can also provide dealer/service options as shown in FIG. 7C. If desired, the user can allow a dealer/service provider full access to most or many of the control features of the pool or spa.

Yet another application for the system 50 is in beta testing of pools or spas by manufacturers of various systems or subsystems used with the pools or spas, e.g. control systems. The system 50 provides an efficient technique to monitor pool/spa conditions remotely, instead of requiring manual monitoring of a beta site.

It is understood and intended that the above-described embodiments are merely illustrative of the possible specific embodiments which may represent principles of the present invention. Other arrangements may readily be devised in accordance with these principles by those skilled in the art without departing from the scope and spirit of the invention.

What is claimed is:

1. Apparatus for remotely monitoring and controlling water parameters in a pool or spa bathing installation including a recirculating water flow path, comprising:
a plurality of sensors for monitoring of a plurality of bathing installation parameters;
an on board electronic pool/spa control system operatively connected to a bathing installation water pump for circulating water through the recirculating water flow path and a water heater, said control system in electrical communication with said sensors for receiving data signals indicative of the monitored water installation parameters, said control system configured to selectively generate control signals to one or more bathing installation control devices including said pump and said heater to affect a change in said bathing installation parameters;
a remote web server;
a dedicated network interface circuit;
a data communication link between said on board electronic pool/spa control system and said dedicated network interface circuit for carrying data signals and command signals; and
wherein said dedicated network interface circuit is adapted to provide a web-based Internet connection to said remote web server for transmitting said data signals to said remote web server for collection, storage and processing on said remote web server, and for transmitting commands received from said remote web server to said on board electronic pool/spa control system for controlling said bathing installation control devices.

2. The apparatus of claim 1, further comprising means connected by an Internet connection to the remote web server for remotely viewing a current operational state of the bathing installation.

3. The apparatus of claim 1, further comprising means connected by an Internet connection to the remote web server for remotely viewing the data stored on the remote server in the form of a graph, chart, or table.

4. A method for remotely monitoring and controlling a pool or spa bathing installation including a recirculation water flow path and an on board electronic pool/spa control system, said method comprising:
collecting bathing installation status and parameter data regarding the pool or spa bathing installation at the on board electronic pool/spa control system;
providing a data communication link between the on board electronic pool/spa control system and a dedicated network interface circuit adapted to provide an Internet connection;
transmitting the bathing installation status and parameter data over said data communication link and over said Internet connection from said on board electronic pool/spa control system to a remote web server for storage and processing at the remote web server;
accessing the remote web server by a remote device connected to the Internet to access the bathing installation status and parameter data; and
transmitting control commands from the remote web server to the on board electronic pool/spa control system through the Internet, the dedicated network interface circuit and the data communication link to direct the on board pool/spa electronic control system to affect a change in said bathing installation status.

5. The method of claim 4, further including accessing the remote web server by use of an Internet browser.

6. The method of claim 4, further comprising remotely accessing the remote server to view a current operational state of the bathing installation.

7. The method of claim 4, further comprising remotely viewing the data stored on the remote server in the form of a graph, chart, or table.

8. A method of monitoring and controlling pool water parameters over the Internet, including:
monitoring said water parameters at said pool by a web-enabled on board electronic pool control system, and detecting an error condition in at least one water parameter range;
transmitting said parameters to a web server connected to the Internet at a selectable interval;
storing said parameters on said web server; making a connection request to the web server from a browser running on a remote device connected to the Internet, and authenticating the connection request by entry of a uniquely assigned password for the pool;
viewing said parameter information stored on said web server on the remote device;
transmitting a command from the remote device to said web server in response to said viewing;

transmitting a command from said web server to said web-enabled on board electronic pool control system at said pool to cause one or more items of pool equipment to take a desired action affecting said water parameter; and generating from said web server or said web-enabled on board electronic pool control system or both said web server and said web-enabled on board electronic pool control system an error alert when said water parameter is outside said range.

9. A method for remotely monitoring and controlling water parameters in a bathing installation including a recirculating water flow path, a pump for pumping water through the water flow path and a heater for heating water, comprising:

providing a sensor for monitoring a water installation parameter;

providing an on board electronic bathing installation control system in communication with said sensor for receiving data signals indicative of the monitored water parameter, said control system configured to selectively generate control signals to control a device related to said parameter;

providing a remote web server;

providing a remote control device; and providing a dedicated network interface circuit for providing an Internet connection between said remote web server and said electronic bathing installation control system;

wherein implementation of the method comprises the steps:

i) transmitting data related to said water parameter from said electronic bathing installation control system through said dedicated network interface circuit to said remote web server for collection and storage;

ii) making a connection request to the web server from a browser running on said remote device connected to the Internet, and authenticating the connection request by entry of a uniquely assigned password for the bathing installation, and viewing said data related to said water parameters by said remote control device;

iii) transmitting a command from said remote control device to said remote web server in response to said viewing;

(iv) transmitting said command from said remote server to said electronic bathing installation control system for controlling said electronic bathing installation control system to affect a change in said parameter.

10. The method of claim 9, wherein a web browser is used for said viewing of said data related to said water parameter.

11. The method of claim 10, further including updating said data related to said water parameter in real-time using a Java applet.

12. The method of claim 10 including providing a pool as said bathing installation.

13. The method of claim 9 including providing a spa as said bathing installation.

14. A method of monitoring and controlling a spa or pool system remotely, comprising:

establishing a data link between a home computer network and an electronic controller of the spa or pool system;

establishing an Internet connection between a remote web server and the electronic controller through the home network;

transferring data indicative of operational and diagnostic information of the spa or pool system from the electronic controller via the Internet connection to the remote web server for storage and processing;

establishing an Internet connection between the remote web server and a remote computer station or web enabled remote control device;

logging into the remote web server using the remote computer station;

viewing said uploaded data using a graphical user interface on a display device at the remote computer site or web enabled remote control device by a spa user, spa owner or spa service personnel, said uploaded data including data representative of real time and historical operational data regarding the monitored spa or pool system; and transmitting commands from said remote computer station or the web enabled remote control device through said remote web server and said home computer network to said electronic controller to cause the electronic controller to control one or more spa or pool devices or a water parameter of the spa or pool.

15. The method of claim 14, wherein said establishing a data link between a home computer network and an electronic controller of the spa or pool system comprises establishing a wireless data link between said home computer network and said electronic controller.

16. A method of monitoring and controlling a spa or pool system remotely, comprising:

establishing a data link between a home computer network and an electronic controller of the spa or pool system;

establishing an Internet connection between a remote web server and the electronic controller through the home network;

transferring data indicative of operational and diagnostic information of the spa or pool system from the electronic controller via the Internet connection to the remote web server for storage and processing;

establishing an Internet connection between the remote web server and a remote computer station or web enabled remote control device;

logging into the remote web server using the remote computer station;

viewing said uploaded data using a graphical user interface on a display device at the remote computer site or web enabled remote control device by a spa user, spa owner or spa service personnel, said uploaded data including data representative of real time and historical operational data regarding the monitored spa or pool system; and transmitting commands from said remote computer station or the web enabled remote control device through said remote web server and said home computer network to said electronic controller to cause the electronic controller to control one or more spa or pool devices or a water parameter of the spa or pool; and wherein said transferring data indicative of operational and diagnostic information of the spa or pool system comprises:

transferring data indicative of a spa cover alarm notification.

17. A method of monitoring and controlling a spa or pool system remotely, comprising:

establishing a data link between a home computer network and an electronic controller of the spa or pool system;

establishing an Internet connection between a remote web server and the electronic controller through the home network;

transferring data indicative of operational and diagnostic information of the spa or pool system from the electronic controller via the Internet connection to the remote web server for storage and processing;

establishing an Internet connection between the remote web server and a remote computer station or web enabled remote control device;

logging into the remote web server using the remote computer station;

viewing said uploaded data using a graphical user interface on a display device at the remote computer site or web enabled remote control device by a spa user, spa owner or spa service personnel, said uploaded data including data representative of real time and historical operational data regarding the monitored spa or pool system; and transmitting commands from said remote computer station or the web enabled remote control device through said remote web server and said home computer network to said electronic controller to cause the electronic controller to control one or more spa or pool devices or a water parameter of the spa or pool; and wherein said transferring data indicative of operational and diagnostic information of the spa or pool system comprises;

transferring data indicative of a pool gate alarm notification.

18. A method of monitoring and controlling a spa or pool system remotely, comprising:

establishing a data link between a home computer network and an electronic controller of the spa or pool system;

establishing an Internet connection between a remote web server and the electronic controller through the home network;

transferring data indicative of operational and diagnostic information of the spa or pool system from the electronic controller via the Internet connection to the remote web server for storage and processing;

establishing an Internet connection between the remote web server and a remote computer station or web enabled remote control device;

logging into the remote web server using the remote computer station;

viewing said uploaded data using a graphical user interface on a display device at the remote computer site or web enabled remote control device by a spa user, spa owner or spa service personnel, said uploaded data including data representative of real time and historical operational data regarding the monitored spa or pool system; and transmitting commands from said remote computer station or the web enabled remote control device through said remote web server and said home computer network to said electronic controller to cause the electronic controller to control one or more spa or pool devices or a water parameter of the spa or pool; and wherein said transferring data indicative of operational and diagnostic information of the spa or pool system comprises:

transferring data indicative of a ground fault circuit interrupter (GFCI) trip or power down notification.

* * * * *